United States Patent [19]

Holmes et al.

[11] 4,017,263
[45] Apr. 12, 1977

[54] APPARATUS FOR SULFURIC ACID CATALYZED ALKYLATION PROCESS

[75] Inventors: Jeffrey W. Holmes, Sedro-Woolley, Wash.; Bruce K. Purcell, Baton Rouge, La.; William F. Franz, Cardiner; Edward L. Cole, Fishkill, both of N.Y.

[73] Assignee: Texaco Inc., New York, N.Y.

[22] Filed: Oct. 18, 1974

[21] Appl. No.: 515,942

[52] U.S. Cl. .................. 23/288 E; 23/288 K; 260/683.61

[51] Int. Cl.² .................. B01J 8/08; C07C 3/54

[58] Field of Search .......... 23/288 K, 288 E, 260; 260/683.41, 683.61, 683.63, 683.49, 683.48; 210/512 R

[56] References Cited

UNITED STATES PATENTS

| | | | |
|---|---|---|---|
| 2,536,515 | 1/1951 | Penick | 260/683.48 |
| 2,714,116 | 7/1955 | Teichmann et al. | 23/288 E UX |
| 3,234,301 | 2/1966 | Goldsby | 260/683.61 |
| 3,281,213 | 10/1966 | Waddill | 260/683.48 X |
| 3,456,033 | 7/1969 | Borst, Jr. | 260/683.48 |
| 3,485,362 | 12/1969 | Spruyt et al. | 210/512 R X |
| 3,485,893 | 12/1966 | Mayhue | 23/238 E UX |
| 3,489,680 | 1/1970 | Snavely | 210/512 R |
| 3,639,372 | 2/1972 | Haynes, Jr. et al. | 23/260 |
| 3,697,230 | 10/1972 | Fyjimoto et al. | 23/260 X |
| 3,701,793 | 10/1972 | Schmidt et al. | 23/288 E UX |
| 3,793,259 | 2/1974 | Brinkmann et al. | 23/288 K |
| 3,855,344 | 12/1974 | Jones | 260/683.49 X |
| 3,925,501 | 12/1975 | Putney et al. | 260/683.48 |

Primary Examiner—Morris O. Wolk
Assistant Examiner—Michael S. Marcus
Attorney, Agent, or Firm—Thomas H. Whaley; Carl G. Ries; Douglas H. May, Jr.

[57] ABSTRACT

Improved alkylation reactor and reaction emulsion phase separation apparatus is described. Such apparatus is particularly useful in sulfuric acid catalyzed alkylation of isoparaffin with olefins for production of high octane value alkylate.

3 Claims, 1 Drawing Figure

APPARATUS FOR SULFURIC ACID CATALYZED ALKYLATION PROCESS

BACKGROUND OF THE INVENTION

This invention relates to a process for alkylating an alkylatable isoparaffin hydrocarbon with olefin hydrocarbons. More specifically, this invention relates to apparatus useful for producing alkylated hydrocarbon product from isoparaffin and light olefin reactants utilizing sulfuric acid alkylation catalyst under alkylation reaction conditions including short contact time of hydrocarbon and acid catalyst with substantially no backmixing of the reaction mixture within the reaction zone. This invention further relates to apparatus useful for producing alkylated hydrocarbons having superior quality as components for motor fuels, as compared to products produced by previously employed alkylation processes.

Alkylation of isoparaffin hydrocarbons such as isobutane, isopentane and the like with olefinic hydrocarbons such as propylene, butylenes, amylenes, and the like, is well-known as a commercial method for producing gasoline boiling range hydrocarbons. The $C_5$–$C_{10}$ carbon number range alkylated hydrocarbon products of such alkylation reactions are particularly useful as motor fuel blending stock because of their high motor octane and research octane values. The selectivity of commercial akylation processes for highly branched isomers of alkylated hydrocarbons determines the maximum product octane values obtainable. Consequently, process apparatus configurations and reaction conditions are being actively sought which favor formation of the highly branched alkylate isomers and which impede side reactions such as olefin polymerization, polymer cracking and isomerization. The olefin polymers and their cracked products have substantially lower octane values than alkylate hydrocarbons of similar molecular weight.

Good contact of reactant isoparaffin and olefin hydrocarbons with alkylation catalyst under alkylation reaction conditions is critical to production of desirable high octane alkylate hydrocarbons. In alkylation reactions employing sulfuric acid as catalyst, the olefin reactants are substantially more soluble in the acid catalyst phase than are isoparaffin reactants. Since olefin hydrocarbons will undergo polymerization reactions in the presence of the 88–98 percent sulfuric acid solutions commonly employed as alkylation catalysts, operating conditions must be selected to insure good contact of olefin with isoparaffin in the presence of sulfuric acid catalyst so that alkylation reactions will occur in preference to olefin polymerization reactions. In currently employed liquid phase alkylation processes this contact of olefin and isoparaffin is obtained by employing isoparaffin in substantial stoichiometric excess to olefin and subjecting the olefin-isoparaffin-sulfuric acid reaction mixtures to high shear mixing such that emulsions of hydrocarbon and acid are formed. Volume ratios of isoparaffin to olefin charge of from 2/1 to 20/1 are employed to insure the availability of isoparaffin for reaction with the olefin. Isoparaffin to olefin volume ratios of 4/1 and greater are preferred.

Generally, it is preferred that the acid phase be maintained as the continuous phase in the reaction emulsions formed such that the hydrocarbon is present as small droplets suspended in the acid phase. Sulfuric acid catalyst concentrations of 40 volume percent and above in an alkylation reaction mixture may result in acid continous emulsions. Consequently acid concentrations in the range of 40–70 volume percent of an alkylation reaction emulsion are preferred. It has, however, been disclosed that hydrocarbon continuous emulsions of isoparaffin and olefin hydrocarbon with sulfuric acid may be employed as alkylation reaction mixtures, and acid concentrations as low as 10 volume percent in the reaction mixture have been successfully employed.

Reaction temperatures found acceptable in the prior art for sulfuric acid catalyzed alkylation of isoparaffin with olefin are in the range of about $-20°$ to about $100°$ F, with reaction temperatures in the range of about $40°$–$60°$ F being preferred. Such akylation reactions are exothermic. Therefore, the reaction mixture is commonly cooled in the reaction zone to maintain the desired reaction temperatures. Cooling by both direct and indirect heat exchange techniques is commonly practiced. One widely practiced technique is to recover the hydrocarbon phase of a reaction mixture and vaporize a portion of the unreacted isoparaffin at reduced pressure and about adiabatic conditions, thereby substantially reducing the temperature of the unvaporized portion of the hydrocarbon phase. This cold liquid hydrocarbon is then used to cool additional reaction mixture in the reaction zone by indirect heat exchange means.

Alkylation reactions of isoparaffins with olefins have been carried out in both the vapor phase and the liquid phase. In the present application, only those reactions carried out in the liquid phase are under consideration. Therefore, reaction pressures sufficient to maintain reactants in the liquid phase at reaction temperatures are required. Consequently, pressures of from about atmospheric to about 100 psig, or higher are commonly employed in such akylation reactions. Pressures above those required to maintain reactants in the liquid phase have no noticeable effect upon the akylation reaction.

Commercial apparatus commonly employed for sulfuric acid catalyzed alkylation of isoparaffin with olefin comprise backmixed reactor vessels equipped with high shear mixing devices such as impellers. Such reaction vessels are sized to provide sufficient residence time for conversion of substantially all olefin with the reaction zone. The high shear mixing is provided to insure good contact of isoparaffin and olefin reactant in the presence of sulfuric acid catalyst. As olefins are substantially more soluble in sulfuric acid catalyst than are isoparaffins, and since olefins tend to polymerize in the presence of the sulfuric acid catalyst, high shear mixing of the reaction mixture to insure good contact of isoparaffin with olefin is critical to production of a high-octane alkylate product. Consequently, substantial amounts of power are consumed in operation of the high shear mixers to provide the required good mixing of reactants. This degree of mixing of a backmixed reactor results in an almost homogeneous reaction mixture, with olefin concentration about equal throughout the reactor volume. As it is desirable to effect essentially complete olefin conversion in the reaction zone for production of higher octane alkylated product, olefin concentration is quite low throughout the reaction vessel.

In commercial processes, reaction emulsion effluent from such back-mixed reactors discharges into settling vessels wherein hydrocarbon phase, comprising unreacted isoparaffin and alkylated hydrocarbon, separates from sulfuric acid catalyst phase by gravity separation. Separated hydrocarbon phase is fractionated to recover alkylate product and isoparaffin. Separated acid phase and isoparaffin fraction are returned to the alkylation reactors for contact with additional isoparaffin and olefin reactants.

In addition to processes employing backmixed reactors and high shear mixers, liquid phase processes for alkylation of isoparaffins with olefins in the presence of acid alkylation catalysts and employing nonback mixed, or tubular, reactors have been proposed. For example, see U.S. Pat. Nos. 3,213,157; 3,169,153; 2,910,522; 3,000,944; and 3,456,033. The processes employ about the same reaction temperatures and pressures, ratios of reactants and catalysts, etc., as employed in commercial backmixed reactor processes. The advantages of nonback mixed reactors include lower equipment cost and improved alkylate octane value over backmixed reactor systems. The major disadvantage is the difficulty of maintaining the reaction emulsion without phase separation, throughout the length of the nonback mixed reactors. Such nonbacked mixed reactors may comprise either vertical or horizontal tubular configurations. Generally, isoparaffin and olefin reactants are mixed with acid catalyst at the inlet of such tubular reactors and reaction mixtures comprising unreacted isoparaffin, alkylated hydrocarbon product and acid catalyst are withdrawn from the outlet of the tubular reactors into settling tanks. In the settling tanks, hydrocarbon phase comprising isoparaffin and alkylate hydrocarbon is separated by gravity settling from acid catalyst phase. Hydrocarbon phase from the settling tank is fractionated to recover alkylate hydrocarbon product and isoparaffin. The isoparaffin fraction and acid-catalyst phase are returned to the inlet of the tubular reactors for contact with additional isoparaffin and olefin reactants.

The prior art discloses that such alkylation processes employing nonbacked mixed reactors are effective for improving alkylate quality and octane value when acid catalysts are used in which substantial amounts of isoparaffin hydrocarbons may be dissolved. Hydrogen fluoride, which will absorb about 2.7 weight percent isobutane at 80° F, is particularly effective in such alkylation processes. On the other hand, alkylation processes, employing acid catalysts which do not absorb a substantial amount of isoparaffin reactant do not produce an improvement in alkylate quality and octane number. For example, nonbacked mixed processes employing sulfuric acid, which only absorbs about 0.1 percent isobutane at 80° F, are not as efficient and do not produce alkylate of improved quality and octane value, as compared to backmixed alkylation processes.

SUMMARY OF THE INVENTION

Now, according to the method of the present invention, we have discovered improved apparatus for alkylating isoparaffin hydrocarbon with olefin hydrocarbon in the presence of sulfuric acid alkylation catalyst employing a nonback mixed tubular reactor.

Advantages of the present invention include the economic savings of reduced equipment and cost and reduced power requirements for processes employing the tubular reactor apparatus as compared to backmixed alkylation processes employing high shear mixing. Additionally, the apparatus of the present invention enables production of alkylate of improved quality and octane value in sulfuric acid catalyzed alkylation processes.

These advantages and others will be described more fully in the detailed description of the invention which follows.

DETAILED DESCRIPTION OF THE INVENTION

Alkylation processes which are to be performed in the improved apparatus of the present invention are those wherein isoparaffin hydrocarbons such as isobutane, isopentane, isohexane, etc. are alkylated with olefin hydrocarbons such as propylene, butylene, pentylenes, etc. Preferably, isobutane is selected as the isoparaffin reactant and olefin reactant is selected from propylene, butylenes, and mixtures thereof. Olefin hydrocarbons in the presence of sulfuric acid alkylation catalysts tend to undergo polymerization reactions as well as the desirable alkylation reactions with isoparaffin hydrocarbons. In order to increase selectivity of olefin conversion to alkylate hydrocarbons, a substantial stoichiometric excess of isoparaffin reactant is desirable. Liquid volume ratios of isoparaffin to olefin of from about 2/1 to about 20/1 are contemplated in the present invention. Preferably, isoparaffin to olefin ratios of at least 4/1 are employed. Reactant hydrocarbon charge streams normally employed in commercial alkylation processes are derived from refinery process streams and may contain small amounts of impurities such as n-butane, propane, etc. Such impurities are undesirable in large concentration as they occupy alkylation reactor volume, thus decreasing reactor capacity available for the desired reactants. Consequently, process charge streams and/or recycle streams are usually fractionated to remove a substantial portion of such paraffinic impurities.

Alkylation catalysts contemplated for use in the apparatus of the present invention comprise from about 88 weight percent to about 98 weight percent $H_2SO_4$, preferably from about 96 weight percent to about 88 weight percent $H_2SO_4$. At $H_2SO_4$ concentrations above 98 weight percent, the rate of the alkylation reaction decreases and the octane value of alkylate product decreases. At $H_2SO_4$ concentrations below about 88 weight percent, olefin polymerization reactions increase, thus reducing the octane value of the alkylate product. For an effective alkylation catalyst, some water and acid oil must be present with the $H_2SO_4$. That is, fresh $H_2SO_4$ of about 98 weight percent concentration containing about 2 weight percent $H_2O$ has little activity as an alkylation catalyst, and an induction period of contact with hydrocarbon reactant under alkylation reaction conditions is necessary to promote the catalyst activity. During this induction period, acid oils which are high molecular weight reaction products of $H_2SO_4$ and hydrocarbon reactants, are generated. Thus an effective alkylation catalyst will comprise from about 88–98 weight percent $H_2SO_4$, from about 1–8 weight percent $H_2O$ and from about 1–6 weight percent acid oils. In addition, a small amount of a compound for increasing solubility of isoparaffin in sulfuric acid catalysts is helpful when using the tubular reactors of the present invention. With such sulfuric acid catalysts comprising $H_2SO_4$, $H_2O$ and acid oils, solubility of isoparaffin in the catalyst phase is quite low, while olefins are substantially soluble in the catalyst. Consequently, in commercial processes, high shear mixing is employed such that an emulsion of hydrocarbon and acid catalyst is formed to insure contact of isoparaffin and olefin reactants in the presence of the catalyst phase. If such mixing is not provided, then isoparaffin will not effectively contact olefin absorbed in the acid catalyst and olefin will tend to polymerize rather than alkylate with such isoparaffin. Such olefin polymers produce heavy alkylate of $C_9$ and greater carbon number having low octane value. Olefin polymers also crack in the presence of acid catalyst producing light alkylate of $C_5$–$C_7$ carbon number, which likewise has low octane value. For these reasons, commercial alkylation processes for alkylation of isoparaffins with olefin in the presence of sulfuric acid have not been successful in nonback mixed, or tubular, reactors without extraneous high shear mixing to maintain hydrocarbon-acid catalyst emulsions. However, we have discovered, when solubility of isobutane in sulfuric acid alkylation catalyst is increased to about 1 volume percent or more, high quality alkylate of high octane value can be produced in nonbacked mixed reactors wherein no extraneous mixing is provided.

One group of compounds which may be employed advantageously for improving solubility of isoparaffins in sulfuric acid catalyst are amphiphilic compounds which form association colloids or micelles in acid solutions. Amphiphilic compounds are chemical compounds the molecules of which possess distinct regions of hydrophobic and hydrophilic character. In acid solutions, aggregations of the amphiphiles form spherical micelles in which the hydrophobic portion of the amphiphiles are located in the interior of the micelle and the hydrophilic portion of the amphiphiles' are at the surface of the micelle. The hydrophophilic portion of a micelle is ionic and/or polar whereas the hydrophobic portion is a non-polar hydrocarbon radical, preferably comprising a straight chain of 8 to 20 carbon atoms. The hydrocarbon radicals, when forming the interior of the micelle, are capable of taking into solution the non-polar isoparaffin reactants. Thus, the micelle forming amphiphilic compounds bring non-polar isoparaffin reactants into solution with the polar sulfuric acid catalysts. The micelles formed are not static species, but rather exist in dynamic equilibrium with the associated polar and non-polar molecules. Consequently, micelles are constantly formed and disassociated, bringing into solution with the acid catalyst and releasing it for contact with olefin reactant under conditions favorable for alkylation reactions to proceed.

A variety of amphiphilic compounds are known to form micelles in solution. These are of three classes: cationic, anionic and nonionic. For use in the present invention, such amphiphilic agents must form micelles and must be reasonably table in acid solution. Examples of compounds which are capable of forming micelles and which are known to enhance acid catalyzed alkylation reactions include: N-(alkyl) benzene sulfonamides; N-(alkyl) alkyl sulfonanides, alkyl sulfonium salts, alkyl phosphonium salts, alkyl benzene sulfonic acids, aliphatic amines, and N'NN" tris (alkyl) phosphonic triamides, alkyl ammonium salts, and salts of alkyl sulfates. It has been found necessary that such amphiphilic compounds contain at least one aliphatic alkyl radical of 8 to 24 carbon atoms. The total number of carbon atoms may be from 8 to 60. Amphiphilic compounds which are preferred in the practice of the present invention are N-(alkyl) benzene sulfonamides where the (alkyl) radical is straight chain having from about 10 to 20 carbon atoms, and N-(alkyl) alkyl sulfonamides wherein the (alkyl) attached to the nitrogen atom is a straight chain having from 10 to 20 carbon atoms and the alkyl radical attached to the sulfur atom is a paraffin or cyclo-paraffin radical having from 1 to 6 carbon atoms. A particularly preferred amphiphilic compound is N-(octadecyl) benzene sulfonamide. In addition to a capability for forming micelles in acid solution, such amphiphilic compounds in sufficient concentration tend to form emulsions of acid catalyst and hydrocarbon reactants. Should the concentration of such amphiphilic compounds be too great, the emulsions formed are rather stable and separation of acid catalyst from hydrocarbon is hindered. Rapid separation of alkylation reaction emulsion into a hydrocarbon phase and an acid phase is desirable for effective processing of the hydrocarbon, for recovery of the alkylate product, and for recycle of the separated acid phase as catalyst to the alkylation reaction zone. In view of the emulsion forming tendencies of such amphiphilic compounds the maximum amount of such compounds used must be carefully controlled. Thus, not more than about 0.5 weight percent of a selected amphiphilic compound should be incorporated into a sulfuric acid alkylation catalyst in order to avoid formation of stable hydrocarbon-acid emulsions. Preferably, not more than about 0.1 weight percent of the selected amphiphilic compound is employed with the sulfuric acid catalyst. The amount of select amphiphilic compounds must be equivalent at least about 0.0005 weight percent of the sulfuric acid catalyst in order to obtain any substantial benefit in an alkylation process.

Temperatures which may be used in alkylation processes performed in the apparatus of the present invention are in the range of from about $-20°$ C to about $100°$ F. Lower temperatures favor alkylation reactions of isoparaffins with olefins over competing olefin polymerization reactions. However, over all reaction rates decrease at lower temperatures. Preferred alkylation reaction temperatures in the range of from about $40°$–$70°$ F, provide good selectivity for alkylation of isoparaffin with olefin at an acceptable reaction rate.

Superatmospheric reaction pressures sufficient to maintain all reactants in the liquid phase are required. Reaction pressures of from about 10 to about 200 psig and higher may be used. Additionally, when the centrifugal separation device is a liquid cyclone, it is advantageous for the pressure to be sufficiently high to provide kinetic energy for separation of the reaction emulsion into a hydrocarbon phase and an acid phase. Pressures of 50–500 psig, or higher are adequate for effecting such phase separation in a liquid cyclone.

Residence time of reaction emulsion, comprising reactant hydrocarbons, acid catalyst and alkylate hydrocarbon in the reaction zone is commonly expressed as olefin space velocity. That is, as volumes of olefin per hour per volume of catalyst. In the present invention olefin space velocities in the range of from about 0.05 to about 1.0 volumes olefin per hour per volume of catalyst may be employed. When the volume ratio of isoparaffin to olefin is in the range of 2/1 to 20/1 and the reactant emulsion comprises 40–70 volume percent acid catalyst within this range substantially all the olefin is converted in the reaction zone. At higher olefin space velocities, all the olefin may not react in the reaction zone. At low-space velocities side reactions, such as cracking, may become significant. Reactants should be maintained in the reaction zone only for a residence time sufficient for conversion of the olefin reactant at the selected reaction conditions. We have also discovered that the hydrocarbon phase comprising unreacted isoparaffin and alkylate product should be separated from the alkylation acid catalyst as soon as possible after the reaction mixtures leaves the reaction zone. A preferred embodiment of the present invention incorporates means for rapid separation of the reaction effluent into hydrocarbon phase and acid phase, and withdrawal of the separated phases without prolonged contact such as is presently experienced in acid settler drums employed in presently utilized processes. That is, we have discovered that limiting contact of hydrocarbon reactant and products with acid catalyst to as nearly as possible the time required for conversion of olefin reactant substantially improves the quality and octane value of the alkylate product.

In the present invention, a nonback mixed reactor is contemplated. Extraneous backmixing of reactants in the reaction zone is not contemplated. We have discovered, that by employing the apparatus of the present invention isoparaffin hydrocarbons may be alkylated with olefin hydrocarbons in the presence of sulfuric acid alkylation alkylation catalyst in a nonback mixed, or tubular, reactor without high shear mixing in the reaction zone. This result is unexpected for heretofore it has been experienced that high shear mixing of the reaction emulsion is required in a backmixed reactor to maintain good contact of isoparaffin and olefin in the presence of sulfuric acid alkylation catalyst. Addition of selected micelle forming amphiphilic compounds, as hereinabove described, to the sulfuric acid alkylation catalyst substantially improves contact of isoparaffin hydrocarbon with olefin hydrocarbon in intimate contact with the sulfuric acid catalyst.

As is discussed herein, the alkylation reaction is much favored by establishing a reaction emulsion comprising reactant isoparaffin hydrocarbons suspended in a continuous sulfuric acid catalyst phase. Although in the present invention we do not contemplate the necessity of providing high shear mixing in the reaction zone to maintain such an emulsion, we do find it necessary to charge reactants and catalyst to the reactor as such an emulsion. Such an emulsion of isoparaffin, olefin and sulfuric acid catalyst containing an amphiphilic compound may readily be established with conventional mixing equipment. For example, the emulsion may be formed by charging the reactants and catalyst, in the desired ratios as described herein, to mixing devices such as mixing valves, centrifugal mixing pumps, high shear centrifugal mixers, turbine mixers, ultrasonic mixers, and other mechanical devices suitable for mixing immiscible liquids. A mixing valve, such as a globe valve may be used to good advantage in the present invention. Preferably, a mixing pump is employed in the present invention. A mixing pump, such as a centrifugal pump, provides sufficient shear to form the desired hydrocarbon in acid emulsion. Additionally, such a pump provides the head required to flow the reactant emulsion through the nonback mixed reactor at flow velocities, as described below, required to maintain the emulsion without phase separation. It is within the contemplation of the present invention that the reactant emulsion discharging from the mixing device, whether mixing valve, mixing pump, or other mixing device, will directly enter the reactor inlet through a minimum length of transition conduit at flow velocities sufficient to prevent any phase separation of the emulsion. Upon mixing reactant isoparaffin and olefin hydrocarbons with the sulfuric acid catalyst, the exothermic alkylation will begin. Consequently, emulsion residence time within the mixing device and transition conduit must be relatively short to prevent an undesirable temperature increase before the reaction emulsion enters the refrigerated reactor. Mixing valves and mixing pumps characteristically have small holding volumes and are amenable to rather close coupling to other process equipment.

In the practice of our invention we use an elongated tubular reactor having inlet and outlet means. The reactor diameter is chosen such that the Reynolds number ($N_{RE}$) of the flowing reaction emulsion is at least about 5000 $N_{RE}$, and preferably is in the range of about 5000–20,000 $N_{RE}$. Higher Reynolds numbers do not contribute substantially to the alkylation reaction. At Reynolds' numbers below about 5000 $N_{RE}$, the reaction emulsion may not be maintained and the reaction emulsion may separate into a hydrocarbon phase and an acid phase. Should separation occur, olefin conversion may be incomplete and/or olefin polymerization reactions may become substantial due to separation of isoparaffin reactants into a separate phase. The length of the tubular reactor is selected to provide the desired olefin space velocity in the range of from about 0.05 to about 1.0 volumes olefin per hour per volume of catalyst. Contact of reactant hydrocarbon with sulfuric acid catalyst for the minimum time required for essentially complete conversion of olefin reactant is preferred.

Reactors in parallel may be employed according to the present invention. By using tubular reactors in parallel, an akylation process with increased capacity may be operated without the necessity of duplicating process equipment collaterial to the tubular reactors.

Reaction temperatures in the range of about −20° F to about 100° F may be employed as hereinabove stated. Reactants may be cooled to the desired reaction temperature prior to being introduced into the reaction zone. However, the alkylation reaction is exothermic and cooling in the reaction zone must be provided to maintain the desired reaction temperature. External, indirect cooling of the tubular reaction zone is contemplated in the present invention. Particularly effective is the use of a cooling jacket surrounding the tubular reactor. That is, a cold fluid flows as refrigerant in a jacket surrounding the tubular reactor, absorbing the heat of the alkylation reaction. In the case of several tubular reactors in parallel, a reactor configuration of the Shell and tube design may be efficiently employed. Flow of the refrigerant fluid may be co-current or countercurrent to the flow of reactant hydrocarbon. Co-current flow will allow some increase in reaction mixture temperature along the length of the reaction tube, such that the reaction temperature is highest in the portion of the reaction tube wherein the concentration of olefin reactant is lowest. This co-current flow of refrigerant fluid and reaction mixture, with the concomitant temperature increase along the reactor length, will encourage complete conversion of olefin at low concentrations. With countercurrent flow of refrigerant fluid and reaction emulsion, temperatures along the length of the reaction zone may be maintained more nearly equal, if desired.

Refrigerant may be a refrigerant fluid separately provided for the purpose, or it may comprise a process stream. For an example of the latter, separated hydrocarbon phase comprising unreacted isoparaffin and alkylate product may be flashed under approximately adiabatic conditions at subatmospheric pressure to vaporize a portion of the isoparaffin. The remaining, unflashed hydrocarbon liquid is cooled by the adiabatic vaporization of the isoparaffin, and this cooled liquid may be used as refrigerant fluid circulated through the cooling jacket for removal of the heat of reaction from the reaction zone.

Efficient transfer of heat from the reaction mixture to the refrigerant fluid is desirable. Particularly useful aids to the transfer of heat from the reaction emulsion to the wall of the reactor are static mixers. Particularly those disclosed in U.S. Pat. No. 3,286,992 and sold under the tradename "Kenics Mixers". These mixers comprise twisted ribbons of metal of substantially the same width as the diameter of the reactor tube. The twisted ribbons are arranged in a configuration which not only insures good transverse mixing of the reaction mixture within the reaction zone, but also transfers reaction mixture from the interior to the wall of the reaction tube, thus bringing all the reaction mixture systematically into contact with the cooled tube wall. Heat transfer from a tube equipped with such static mixers is many times greater than from a tube not so equipped. Other static mixers than these of the "Kenics" design are available, although, the "Kenics" mixer is the simplest of construction and has the lowest pressure drop for an equivalent degree of mixing. In addition to improve heat transfer from the tubular reactor such static mixers substantially aid maintenance of the reaction emulsion without phase separation in the reaction tube. Such static mixers, at usually encountered flow velocities, are not effective for forming an emulsion of hydrocarbon reactants in sulfuric acid catalyst, but are useful for maintaining such an emulsion, once formed. The uses of such static mixers for improving heat transfer from a tube, and for providing substantial mixing of fluids at a very low pressure drop, are well-known and are widely practiced.

In the process of the present invention, liquid reaction emulsion effluent exits the tubular reaction zone at a high velocity required to maintain a Reynolds number of at least 5000 $N_{RE}$ in the reaction zone. The kinetic energy of the flowing effluent is utilized for obtaining rapid separation of the emulsion effluent into a hydrocarbon comprises unreacted isoparaffin and alkylate product, substantially free of acid catalyst. The separated acid phase comprises sulfuric acid alkylation catalyst and a minor amount of hydrocarbon. That is, the separated acid phase comprises about 100-70 volume percent sulfuric acid alkylation catalyst and about 0-30 volume percent hydrocarbon. Additionally, the amphiphilic compound employed with the sulfuric acid alkylation catalyst remains in the separated acid phase. The kinetic energy of the flowing reaction effluent emulsion is utilized for separation of the hydrocarbon and sulfuric acid alkylation catalyst phases in a mechanical separation device employing centrifugal forces, such as a liquid cyclone, centrifuge, etc.

Liquid cyclone separation devices are particularly effective for rapidly separating the heavier acid phase from the lighter hydrocarbon phase. Such a cyclone is basically a centrifugal machine utilizing the forces of gravity for separating two immiscible fluids having different specific gravities. Such gravity force equipment "parts" the immiscible fluids by means of differences in specific gravity. Equipment using gravity forces, including cyclones, can be characterized by the level of the forces developed, residence time provided, and the turbulene created. A settler, for example, allows long residence time and gives essentially quiescent conditions. On the other hand, liquid cyclones develop forces up to 1000 g or more, have very short residence times, and provide turbulent action.

In the case of gravity force machines, ease of separation depends upon Stokes' Laws variables; i.e., separability is directly proportional to the immiscible droplet diameter squared times the specific gravity differential between the immiscible fluids, and is inversely proportional to the viscosity of the continuous fluid.

Although the relationship is valid and straight forward, the variables themselves are difficult to determine, and if known are not directly usable. For instance, an emulsion may contain immiscible droplets of known size suspended in a continuous medium, however deformation of the droplets may impart shapes detrimental to separability. Or, if many droplets are in suspension, they tend to collide and, hence, do not settle well. On the other hand, droplet coalescense, induced or natural, can provide a decided improvement in separability.

The effect of viscosity as a factor on separability is sometimes difficult to determine; under dynamic conditions such as occur in cyclones, viscosity can rarely be measured. For these reasons, then, reliance must eventually be placed upon empirical tests to resolve any given separation problem. However, cyclones for separation of solids from fluids and for separation of fluids from fluids are well-known in the art, and one skilled in the art can make a preliminary judgement as to possible cyclone application by comparing the Stokes' Law Variables of previously tested standard slurries, an the new, untested emulsions.

Such cyclone separators comprise a cyclindrical upper section attached to a conical lower section. The inlet stream enters the cylindrical section tangentially, so that a velocity redistribution is involved, resulting in a tangential velocity component which increases with decreasing radius. The flow path invokes a double vortex, with downward spiraling flow at the outside and upward spiraling flow at the center. Spiral velocities may reach values several times the average velocity in the inlet section. The more dense phase of the inlet stream, by virtue of its interia, will tend to move toward the outside wall and pass downward through the conical section, to be removed into a suitable receiver. The less dense phase will pass upward in the central upward spiral flow to be removed at the top of the cyclone through a tube. The centrifugal separating force, or acceleration may range from about 5 times gravity for large, low resistance units to about 2,500 times gravity for small, high pressure drop units.

One advantage of such a separation device, utilizing centrifugal (or gravity) force to separate the hydrocarbon phase from the acid phase, is the kinetic energy of the reaction zone effluent is effectively used and additional energy need not be expended. Another advantage is, the hydrocarbon phase may be rapidly separated from the acid phase without an extended period of contact such as is experienced in a gravity settling vessel. The overall short contact time of hydrocarbon reactants, and alkylate products with sulfuric acid catalyst in a tubular reactor and centrifugal phase separator contribute materially to the good quality and high octane value of alkylate product. Undesirable side reactions which proceed at slower rates than the alkylation reaction such as cracking, isomerization, polymerization, and self-alkylation reactions are minimized when contact of hydrocarbon and acid catalyst is limited to essentially the time required for conversion of essentially all the olefin reactant.

A third advantage of a mechanical separation device operating upon the principle of centrifugal separation of the hydrocarbon phase and the acid catalyst phase resides in the characteristic of such devices which allows the degree of separation to be closely controlled and varied within a substantial range. That is, by selection of a properly sized separation device for the expected flow of reaction effluent, the hydrocarbon phase may be recovered subtantially free of acid catalyst and the acid phase may be recovered with a controlled hydrocarbon content. For instance, a liquid cyclone is operated such that hydrocarbon phase is withdrawn substantially free of acid, and acid phase is withdrawn at rate to prevent accumulation of acid phase in the cyclone. The rate of acid phase withdrawal may be adjusted to withdraw a volume equivalent only to the volume of acid catalyst entering the cyclone, in which the hydrocarbon content of the acid phase will be quite low, in the range of 0–2 volume percent. Or, if desired, the rate of acid phase withdrawal may be increased to a value somewhat greater than the volume of acid catalyst entering the cyclone in which event the hydrocarbon content of the acid phase will be increased, in the range of 2–30 volume percent. The operation of a sulfuric acid catalyzed alkylation process is substantially improved when acid catalyst phase entering the reaction zone contains a minor portion of hydrocarbon, in the range of 0–30 volume percent and preferably in the range of 3–8 volume percent. The presence of such hydrocarbon in the acid phase improves emulsification of acid phase and hydrocarbon reactants, causing the desired alkylation reactions to predominate over undesired side reactions. By using separation devices operating upon the principle of centrifugal separation of the phases, the hydrocarbon content of the separated acid phase, which is recycled within the alkylation process, may be easily controlled within the desired range.

In operating of such separation devices as described above, we have discovered that separation of acid phase from the hydrocarbon phase can be substantially improved if the reaction emulsion entering the separation device has a hydrocarbon continuous phase with acid catalyst entrained therein. That is, hydrocarbon phase substantially free of acid catalyst is more easily separated from an emulsion wherein the hydrocarbon phase is continuous with small droplets of acid catalyst suspended therein. However, for efficient alkylation of isoparaffin with olefin in a tubular reactor, an emulsion comprising acid catalyst continuous phase is preferred. Acid catalyst continuous phase emulsions with isoparaffin and olefin hydrocarbons which are useful in alkylation reactions may comprise about 40–70 volume percent acid catalyst. We have found that such reaction zone emulsion effluents may readily be converted from acid phase continuous emulsions to hydrocarbon phase continuous emulsions by dilution of the emulsion with additional hydrocarbon to obtain diluted emulsion. Comprising 60 volume percent or more hydrocarbon phase. In the process of the present invention, dilution of the reaction zone effluent emulsion is effectively accomplished by circulating a portion of the separated hydrocarbon phase from the outlet of the separation device for contact with reaction zone effluent emulsion at the inlet of said separation device. By this means an acid phase continuous reaction emulsion may be maintained in the reaction zone, and at the reaction zone outlet the emulsion effluent may be converted to an emulsion with a continuous hydrocarbon phase for more efficient separation.

Hydrocarbon phase from the separation device comprises unreacted isoparaffin hydrocarbon and alkylate hydrocarbon product. This separated hydrocarbon phase may be taken directly to a fractionation zone for recovery of isobutane and alkylate hydrocarbon. Preferably, however, the separated hydrocarbon phase is employed to cool the reaction zone to a desired operating temperature. For cooling, the separated hydrocarbon phase from the separation device is passed through a pressure reducing means such that a substantial portion of the isoparaffin hydrocarbon is flash vaporized under conditions approaching adiabatic and the remaining unvaporized hydrocarbon is thereby cooled to a temperature sufficient to cool the reaction zone. The cold hydrocarbon liquid is then preferably passed in indirect heat exchange with the reaction emulsion in the reaction zone. Preferably, the separated hydrocarbon phase is partially vaporized at subatmospheric pressure such that the remaining unvaporized hydrocarbon liquid has a temperature sufficiently low to insure cooling of the reaction emulsion. Conveniently, subatmospheric pressure may be obtained by such means as vacuum pumps, etc. The vaporized hydrocarbon, which is substantially all isoparaffin, may be condensed and recycled to the inlet of the reaction zone for contact with additional olefin reactant and acid catalyst. The unvaporized hydrocarbon, after being employed to cool the reaction zone, may then be passed into a product recovery zone wherein isoparaffin is separated from alkylate product. Isoparaffin from the product recovery zone may be recycled to the inlet of the reaction zone for contact with additional reactant hydrocarbon.

Separated acid phase from the centrifugal device is preferably recycled as catalyst to the inlet of the reaction zone for contact with additional olefin and isoparaffin reactant. In a continuous process, as acid strength of the alkylation catalyst declines and as water and acid oil impurities increase, a portion of the recycle acid catalyst may be withdrawn from the process and fresh sulfuric acid added to maintain sulfuric acid content of the acid catalyst in the range of about 98–88 weight percent.

Figure 1:
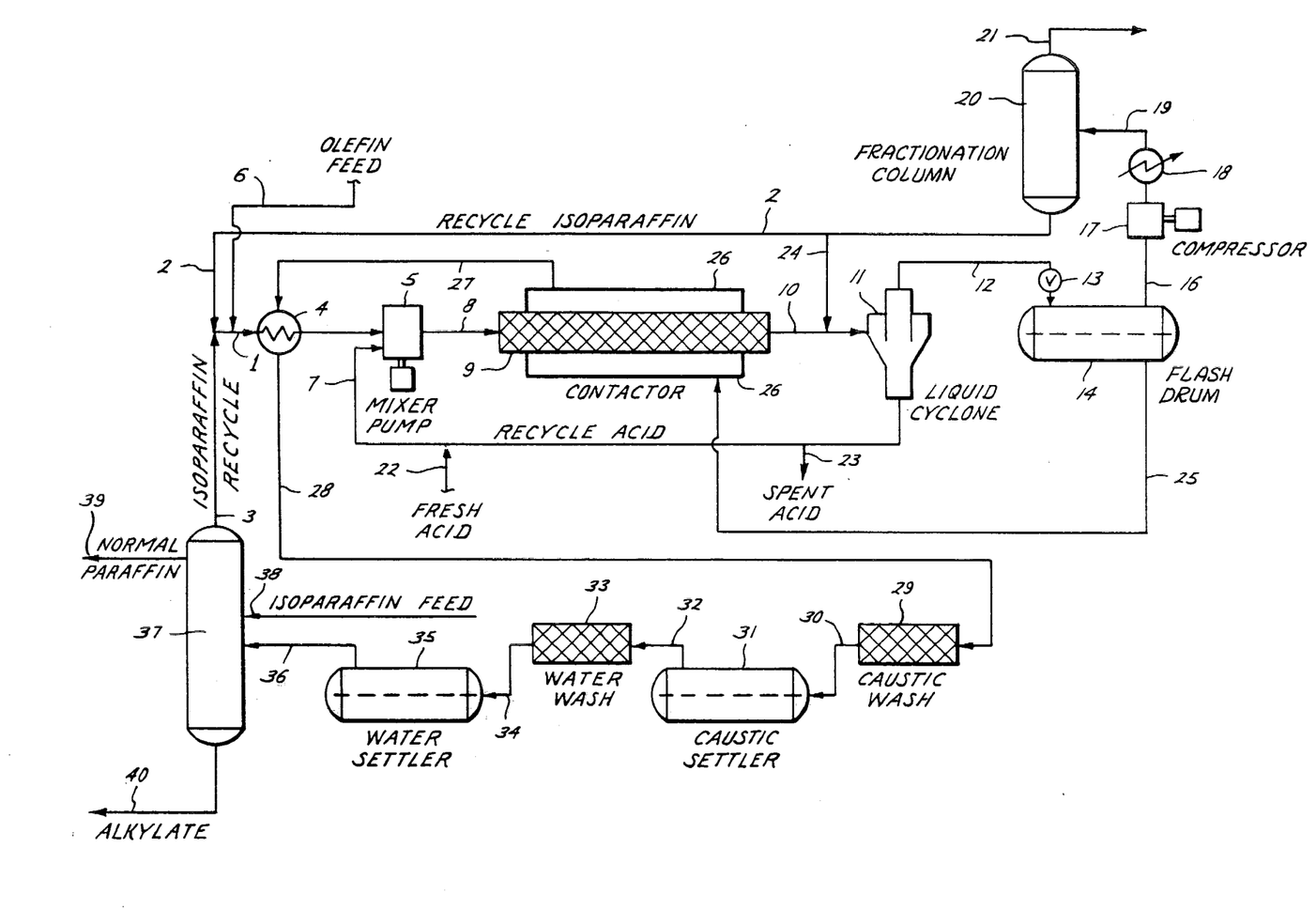
The drawing is a schematic diagram of an alkylation process employing the improved apparatus of the present invention.

In order to better describe the present invention attention is now drawn to the appended drawing. The drawing is a schematic diagram of alkylation process equipment embodying the improvements of the present invention. The drawing, and the detailed description which follows are intended to be illustrative of the invention only, and not intended to limit the scope of the invention which is described in the appended claims.

In the drawing, isoparaffin from line 2 and 3, as will hereinafter be described, is combined in line 1 with olefin feed from line 6 in an isoparaffin olefin volume ratio in the range of 2/1 to 20/1. The isoparaffin olefin mixture from line 1 is cooled in cooler 4, and passes into mixer 5. Sulfuric acid catalyst from line 7 also enters mixer 5. In mixer 5, isoparaffin, olefin, and acid catalyst are mixed to form an emulsion comprising about 40–70 volume percent of a continuous acid catalyst phase, containing about 98–88 weight percent sulfuric acid and from about 0.0005 to about 0.5 weight percent of a micelle forming amphiphilic agent and about 60–30 volume percent of discontinuous hydrocarbon phase. Olefin, being somewhat soluble in the acid phase, is distributed between the hydrocarbon and acid phase. From mixer 5 the emulsion passes via line 8 into tubular reactor 9 through which the reaction emulsion flows with substantially no backmixing. In reactor 9 the emulsion flow at a Reynolds number of at least 5000 $N_{RE}$ for a residence time sufficient to provide an olefin space velocity of from about 0.1 to about 1 volumes olefin per hour per volume of alkylation catalyst (v/v/hr). Temperature of the reaction emulsion is maintained at a selected temperature of from about $-20°$ F to about $100°$ F and at a superatmospheric pressure of about 50 psig to about 20 psig sufficient to maintain all reactants in the liquid phase and provide kinetic energy for separating hydrocarbon phase from acid phase in centrifugal separation device 11, as will hereinafter be described. From reactor 9, reaction emulsion effluent is transferred via line 10 to centrifugal separator 11. Advantageously, for separation of the phases, hydrocarbon from line 24 is mixed with reaction emulsion effluent in line 10 to produce a mixture comprising 40–70 volume percent hydrocarbon phase 60–30 volume percent acid phase, wherein the hydrocarbon phase is continuous.

In the drawing the hydrocarbon-acid catalyst emulsion from line 10 enters centrifugal separator 11, wherein hydrocarbon phase is separated from acid phase by application of centrifugal force to the emulsion. Upon separation, the phases are rapidly removed from centrifugal separator 11 to avoid contact of hydrocarbon with acid catalyst under conditions which promote side reactions such as cracking and isomerization.

In the drawing, separated hydrocarbon phase comprising unreacted isoparaffin and alkylate hydrocarbon passes through line 12 and pressure reducing means 13 into flash drum 14. In flash drum 14, a portion of the hydrocarbon phase is flashed at a subatmospheric pressure under about adiabatic conditions, thereby cooling the unflashed portion of the hydrocarbon liquid to a temperature below the selected reaction temperature to be maintained in reactor 9. From flash drum 14, vaporized hydrocarbon, comprising unreacted isoparaffin as a major component, passes through line 16 and compressor 17 into condensor 18 wherein the hydrocarbon vapor is condensed. From condensor 18, hydrocarbon is charged via line 19 to fractionation column 20 wherein hydrocarbons lower boiling than the isoparaffin hydrocarbon, which may have entered the process as charge stream impurities or be the products of unwanted side reactions, are separated from the isoparaffin hydrocarbon. Such lower boiling hydrocarbons are withdrawn from fractionation column 20 via line 21. Isoparaffin hydrocarbon substantially free of lower boiling hydrocarbon is returned to the process for content with additional olefin via line 2 as hereinabove described.

In the drawing, acid catalyst phase separated from the hydrocarbon phase is centrifugal separator 11, is recycled via line 7 to mixer 5 for contact with additional isoparaffin and olefin reactants, as hereinabove described. Such recycle acid phase consists of about 70–100 volume percent of acid alkylation catalyst and about 30–0 volume percent entrained hydrocarbon. The acid alkylation catalyst comprises about 98–88 weight percent sulfuric acid, about 1–8 weight percent water, about 1–6 weight percent acid oil, and contains from about 0.005 to about 0.5 weight percent of a selected micelle forming amphiphilic agent. Impurities, such as excess water and acid oils are removed from the alkylation process by withdrawing a portion of the recycle acid phase as spent acid, from line 7 via line 23. Fresh acid, comprising 99.5–97 weight percent $H_2SO_4$, and containing about 0.0005 to 0.5 weight percent of a micelle forming amphiphilic agent is added to the acid recycle via line 22. This fresh acid is makeup for the volume of spent acid removed, and serves to maintain acid catalyst $H_2SO_4$ concentration within the desired range.

In the drawing, cold hydrocarbon liquid, comprising isoparaffin and alkylate, from flash drum 14 is passed via line 25 into cooling jacket 26 which surrounds tubular reactor 9. The cold hydrocarbon liquid comprises unreacted isoparaffin hydrocarbon and alkylate hydrocarbon. In cooling jacket 26, the exothermic heat from the alkylation reaction is transferred through the walls of reactor 9 into the cold hydrocarbon, thus maintaining the temperature of the reaction emulsion within the desired temperature range. After absorbing heat from reactor 9, hydrocarbon stream absorbs additional heat from the isoparaffin-olefin stream in cooler 4, as hereinabove described.

In the drawing, from cooler 4 the hydrocarbon stream passes via line 28 to caustic wash zone 29 wherein any entrained acid is neutralized by reaction with caustic solution and from caustic wash zone 29 the mixture of hydrocarbon and caustic solution passes via line 30 into caustic settler 30 wherein the mixture separates by gravity settling into a hydrocarbon phase and a caustic phase. Hydrocarbon phase from caustic settler 31 passes via line 32 into water wash zone 33 wherein the hydrocarbon phase is contacted with water for removal of any entrained caustic. From water wash zone 33, the hydrocarbon-water mixture passes via line 34 to water settler 35 wherein hydrocarbon is separated from water phase by gravity settling. From water settler 35, hydrocarbon passes via line 36 into product fractionation column 37.

In the drawing, isoparaffin feed, to makeup for that consumed in the processes, enters product fractionation column 37 via line 18. In column 37 the water washed hydrocarbon from line 36 and fresh isoparaffin feed are fractionated into an isoparaffin fraction, a normal paraffin fraction having the same molecular weight as the isoparaffin, and an alkylate fraction. The isoparaffin fraction passes from product fractionation column 37 via line 3 into line 1, as hereinabove described, for mixture with the isoparaffin stream from line 2. The normal paraffin fraction, of the same molecular weight as the isoparaffin, is withdrawn from product fractionation column 37 via line 39. The alkylate product fraction, comprising hydrocarbons of molecular weight greater than the isoparaffin, and having a high octane value, is withdrawn from product fractionation column 37 via line 40 for transfer to gasoline blending facilities, not shown.

EXAMPLE I

This example illustrates operation of an alkylation process employing apparatus of the present invention.

Hydrocarbon charge mixture, comprising olefin hydrocarbon, fresh isobutane charge and recycle isobutane, having the composition shown in Table 1 below, is mixed in a centrifugal pump at a rate of 539 bbl/hr. with recycle catalyst emulsion comprising about 8.4 volume percent hydrocarbon and about 91.6 volume percent acid catalyst to form a reaction emulsion comprising 60–62 volume percent acid catalyst.

The acid catalyst comprises about 94 weight percent sulfuric acid, about 2 weight percent water, about 4 weight percent acid oil, and contains 0.015 weight percent of the micelle forming amphiphilic compound N-(octadecyl) benzene sulfonamide.

The reaction emulsion is charged to a tubular reactor cooled by indirect heat exchange with a refrigerant fluid, said tubular reactor having a diameter of six inches and a length of 197 feet. Reaction conditions within the tubular reactor include reactor inlet temperature of 43° F, reactor outlet temperature of 47° F, and reaction emulsion residence time of 30 seconds to provide an olefin space velocity of about 0.60 volumes olefin per hour per volume of acid catalyst. The reaction emulsion is flowed through the tubular reactor at a rate such that the average Reynolds number is 8350 $N_{RE}$. This Reynolds number is well within the turbulent range, thus the reaction emulsion is maintained throughout the length of the tubular reactor without separation of the phase. Reaction effluent from the tubular reactor outlet is mixed with about 500 bbls. per hour of recycle isobutane for conversion of the emulsion from a hydrocarbon in continuous acid phase emulsion to an acid in continuous hydrocarbon phase emulsion which is then passed directly into a 24 inch diameter liquid cyclone for separation into a hydrocarbon phase and an acid catalyst phase. The acid catalyst phase is recycled to the tubular reactor inlet for contact with additional hydrocarbon reactants. About two bbls/hr. of fresh 98 weight percent sulfuric acid is added to the recycle acid stream to maintain the acid concentration therein, and a concomitant amount of acid phase is withdrawn as spent acid.

TABLE 1

| HYDROCARBON FEED COMPOSITION | |
| --- | --- |
| COMPONENT | VOLUME PERCENT |
| $C_2^=$ | 0.7 |
| $C_3^=$ | 0.1 |
| $C_3$ | 4.3 |
| $i-C_4$ | 81.0 |
| $n-C_4$ | 4.0 |
| $i-C_4^=$ | 5.0 |
| $n-C_4^=$ | 4.3 |
| $i-C_5$ | 0.6 |

The separated hydrocarbon phase is fractionated to yield 100 bbl/hour of a stabilized alkylate product having the properties shown in Table 2 below.

TABLE 2

| ALKYLATE PRODUCT PROPERTIES | |
| --- | --- |
| GRAVITY | 70.6 |
| Composition | |
| GC - Weight Percent | |
| $C_4-C_5$ | 11.3 |
| $C_6-C_7$ | 7.1 |
| $C_8$ | 72.9 |
| $C_9+$ | 8.7 |
| RON (clear) | 97.0 |
| MON (clear) | 93.4 |

The foregoing descriptions and example have illustrated improved apparatus for use in sulfuric acid catalyzed alkylation of isoparaffin hydrocarbon with olefin hydrocarbons wherein the alkylation reaction is carried out in a nonback mixed reactor, wherein minor amounts of micelle forming amphiphilic compounds are present in the acid catalyst, and wherein reactant and product hydrocarbon are contacted for only a limited time to produce increased yields to alkylate hydrocarbon having high octane value. It will be apparent that variations and modifications of our process and apparatus included within the scope of the present invention can be similarly employed in the procedures illustrated in the example. Similarly, other isoparaffin and olefin reactants, and other amphiphilic compounds can be employed, and will be apparent to those skilled in the art, it is not intended to limit the foregoing disclosure to the particular features shown.

We claim:

1. Apparatus for alkylating isoparaffin hydrocarbon with olefin hydrocarbon, in the liquid phase, in the presence of sulfuric acid alkylation catalyst, which apparatus comprises:

a. mixing means for forming an emulsion of isoparaffin and olefin reactants and sulfuric acid catalyst;

b. a non-backmixed tubular reactor, having an inlet end, an outlet end and a tubular wall, the inlet of which is in communication with said mixing means, for maintaining the emulsion effluent from said mixing means at alkylation reaction conditions, including a selected temperature of from about −20° F to be about 100° F, an olefin space velocity of from about 0.05 to about 1.0 volumes olefin per hour per volume of acid catalyst and a Reynolds number for said flowing emulsion of at least about 5000 $N_{RE}$;

c. liquid cyclone centrifugal separation means having an inlet in communication with the outlet of said tubular reactor and having a hydrocarbon outlet and an acid catalyst outlet, for rapidly separating reaction emulsion effluent into a liquid hydrocarbon phase comprising unreacted isoparaffin hydrocarbon and alkylate hydrocarbon product, and an acid catalyst phase comprising about 70–100 volume percent acid catalyst and about 30–0 volume percent entrained hydrocarbon;

d. a cooling jacket having inlet and outlet means, surrounding said tubular reactor, defining a confined path for the flow of a refrigerant fluid;

e. a flash drum having an inlet, a top vapor outlet and a bottom liquid outlet, for adiabatically flashing a portion of said separated liquid hydrocarbon phase;

f. first conduit means for conveying separated liquid hydrocarbon phase from said centrifugal separation means to the inlet of said flash drum;

g. a gas compressor, in communication with the top vapor outlet of said flash drum for withdrawing hydrocarbon vapor from said flash drum at a subatmospheric pressure;

h. condensing means in communication with compressor discharge for condensing hydrocarbon vapor from said gas compressor;
i. first fractionation means, in communication with said condensing means, for fractionating condensed hydrocarbon vapor into a first isoparaffin fraction and a fraction lighter than the first isoparaffin fraction;
j. second conduit means for conveying said first isoparaffin fraction from said first fractionation means to said mixing means;
k. third conduit means for conveying cooled, unvaporized hydrocarbon from said flash drum to said cooling jacket inlet;
l. second fractionation means for fractionating separated liquid hydrocarbon phase into a second isoparaffin fraction, a normal paraffin fraction, and an alkylated hydrocarbon fraction;
m. fourth conduit means for conveying liquid hydrocarbon phase from said cooling jacket outlet to said second fractionation means;
n. means for recycling the second isoparaffin hydrocarbon fraction from said second fractionation means into said second conduit means before the inlet of said mixing means for contact with additional reactant hydrocarbons; and
o. means for recycling acid catalyst phase from said centrifugal separation means to the inlet of said mixing means.

2. The apparatus of claim 1 including:
p. fifth conduit means for introducing olefin feed into said second conduit means;
q. indirect heat exchange means for exchanging heat from olefin feed, first isoparaffin fraction and second isoparaffin fraction in said second conduit to the liquid hydrocarbon fraction in said fourth conduit means; and
r. means for removing any sulfuric acid from the liquid hydrocarbon fraction in said fourth conduit means, after said indirect heat exchange means and before said second fractionation means.

3. The apparatus of claim 2 wherein the mixing means is a centrifugal pump.

* * * * *